United States Patent [19]

Ors et al.

[11] Patent Number: 4,651,011
[45] Date of Patent: Mar. 17, 1987

[54] NON-DESTRUCTIVE METHOD FOR DETERMINING THE EXTENT OF CURE OF A POLYMER

[75] Inventors: Jose A. Ors, Solebury Township, Bucks County, Pa.; Suzanne F. Scarlata, South Brunswick Township, Middlesex County, N.J.

[73] Assignee: AT&T Technologies, Inc., Berkeley Heights, N.J.

[21] Appl. No.: 740,155

[22] Filed: Jun. 3, 1985

[51] Int. Cl.⁴ ............................................. G01N 21/64
[52] U.S. Cl. .............................. 250/459.1; 250/458.1; 356/368
[58] Field of Search ............... 250/459.1, 458.1, 358.1; 356/369, 368, 364

[56] References Cited

U.S. PATENT DOCUMENTS

| | | | |
|---|---|---|---|
| 3,679,309 | 7/1972 | Hiragaki et al. | 356/368 |
| 3,912,928 | 10/1975 | Rush et al. | 250/302 |
| 4,511,757 | 4/1985 | Ors et al. | 178/68.5 |
| 4,521,111 | 6/1985 | Paulson, Jr. et al. | 356/367 |
| 4,582,520 | 4/1986 | Sturm | 65/3.43 |
| 4,586,820 | 5/1986 | Yokoyama et al. | 356/317 |

Primary Examiner—Janice A. Howell
Assistant Examiner—Constantine Hannaher
Attorney, Agent, or Firm—J. F. Spivak

[57] ABSTRACT

A non-destructive method for determining the degree of cure of a polymer, e.g., a polymer film, is based upon measuring the degree of free space rotation of a fluorophore added to the polymer system through fluorescent measurements of the fluorophore. The results can be used to control, on-line, the polymerization of the polymer.

14 Claims, 6 Drawing Figures

NON-DESTRUCTIVE METHOD FOR DETERMINING THE EXTENT OF CURE OF A POLYMER

FIELD OF THE INVENTION

This invention relates to a non-destructive method for determining the extent of cure of a polymer. The method is particularly suitable for in-line manufacturing processes wherein polymer films or coatings are cured, for example, in the manufacture of multilayer printed circuit boards.

BACKGROUND OF THE INVENTION

In many manufacturing processes, the ability to repeatedly and uniformly cure a polymer system is highly important, if not critical, to the resultant product. Heretofore, methods for determining the degree of cure were not only time consuming, but were also destructive and could not be applied as an "in-line" process. Examples of such prior art methods are solvent extraction of the polymerized film wherein the quantity of uncured material which is dissolved in the solvent is measured and compared with the total weight of cured and uncured polymer to calculate the % Sol; and glass transition temperature ($T_g$) determinations of the polymer wherein the $T_g$ is directly related to the extent of polymerization.

A major concern in the manufacture of high density multilayer printed wiring boards employing a thin photodefinable polymeric dielectric film to separate conductive layers is the ability to inspect the board prior to operations such as lamination, circuit formation and solder mask application to insure uniformity from board to board and to insure the proper degree of cure has been attained. Conductive paths in the various layers are selectively interconnected by photodefined microvias in the dielectric. The degree of cure achieved in these photodefinable dielectric layers is critical to the proper operation of the multilayer printed circuit board. Also, the ability to successfully inspect the degree of cure of the photodefinable polymer layers used in such boards allows for processing and/or repair schemes which can result in increased product yields.

We have now discovered a non-destructive, optical means, for determining the extent of cure of a polymer which can be operated as an on-line, real-time test during a manufacturing process and can be used to control the process.

SUMMARY OF THE INVENTION

A small amount of a compatible, non-reactive fluorescent material (fluorophore) is included in the polymer system to be cured. The fluorophore in the polymer is excited with linearly or plane polarized actinic radiation having a wavelength that causes the material to fluoresce. The fluorescent emission from the fluorophore is determined both at two predetermined angles with respect to the exciting radiation. The free space of rotation of the fluorescent material in the polymer matrix is determined from these measurements. This determination serves as an accurate non-destructive measure of the degree of cure of the polymer since the ability of the fluorophore to rotate will be reduced as curing and crosslinking of the polymer proceeds. The measured quantities can either be compared with a previously determined standard to obtain an absolute value for the degree of cure, or, can be utilized merely to compare or maintain a uniform degree of cure throughout a manufacturing process.

In addition, the method can be used to control the degree of cure of a polymer by employing an output from the measuring apparatus to a mechanism, such as a comparator, which is coupled to the means is for controlling the degree of cure of the polymer to a predetermined level. For example, the output of the comparator can be coupled with and activate, deactivate or control the curing apparatus so as to control curing parameters such as radiation exposure or power in the case of a photopolymer cured by means of actinic radiation, or thermal cycling in the case of a polymer cured by heat.

DETAILED DESCRIPTION

Figure 1:
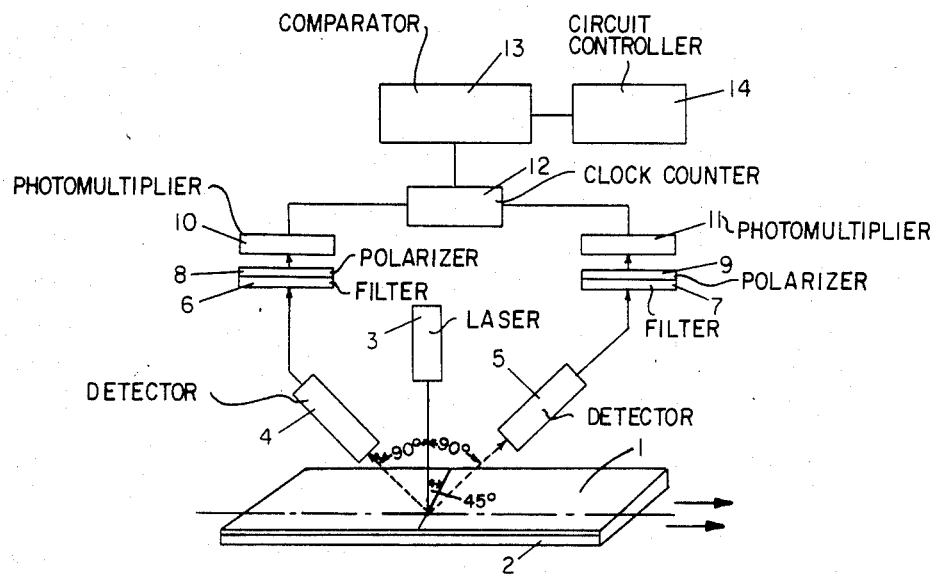
FIG. 1 is a schematic of an apparatus that may be employed for determining the extent of polymerization.

Generally, we have demonstrated that a fluorescent material such as a fluorescent dye dissolved in a monomer, oligomer or polymer can be used to monitor, non-destructively, the degree of cure or polymerization via the fluorescence anisotropy (A) or polarization (p) of the fluorophore by means of an optical inspection system. Further, the system can be used to control the means for and hence, degree of polymerization. Such a scheme is particularly useful for monitoring the cure of a polymer film on a printed circuit board. It should be understood, however, that its use is not so limited and it is, in fact, applicable to determine and/or control the degree of polymerization for any polymer in any environment. It is, however, especially suitable for polymer films. The method is based upon the relationship of the measure of the relative restriction of the fluorophore's rotational motion caused by the changes in the surrounding polymer matrix as curing of the polymer proceeds. As the polymeric material cures, the crosslink density increases resulting in a tighter matrix which restricts the motions of the fluorophore. Loss of rotational freedom will cause an increase in the fluorescence polarization value of the excited fluorophore that will approach its limiting value ($p_o$) as its motion becomes more restricted during the lifetime ($\tau$) of its fluorescent state. When coupled with automatic comparators in a feedback system, as shown in FIG. 1, an on-line evaluation and control of the surface of organic polymeric coatings can be obtained regardless of the substrate used.

Polarization or anisotropy are determined by exciting a fluorescent species with linearly or plane polarized light and measuring the fluorescent emission at fixed angles to the exciting radiation. If the fluorophore is motionless during the lifetime of the excited state, then (p) or (A) is a function of the angle of the absorption and emission dipoles and is termed the limiting polarization ($p_o$) or anisotropy ($A_o$). Rotational motion during the fluorescent lifetime, however, will cause further depolarization. This depolarization can be described by the Perrin equation $$\frac{(1/p - 1/3)}{(1/p_o - 1/3)} = \frac{A_o}{A} = 1 + \frac{RT\tau}{\eta V} \quad (1)$$

where R is the gas constant and T is the absolute temperature, V is the molecular volume and $\eta$ the viscosity. The amplitude of the arc (AMP) that the fluorophore undergoes during rotation can be determined by the following equation $$\frac{(3 \cos^2 \text{AMP}) - 1}{2} = \frac{A}{A_o} \quad (2)$$

Therefore, measuring the anisotropy with respect to $A_o$ will determine the dye's free space of rotation allowed by the polymer matrix, and serve as a measure of cure of the polymer.

Referring to FIG. 1 there is shown a schematic diagram of an apparatus useful for making on-line measurements of a cured polymer film or continuous web 1 on a substrate 2 to determine and/or assure the degree of cure obtained. The apparatus includes a source of linear or plane polarized light having an emission in a region of the spectrum capable of causing fluorescent excitation of a fluorescent material included in the polymer film 1, e.g., a laser 3 or a broad band source with a compatible polarizer and filter which transmits the exciting radiation. The resulting fluorescent output is transmitted through transmission means such as a pair of fiber optic detectors (or collecting lenses), 4 and 5 each situated at an angle of 90° to the incident laser radiation and in the same plane as each other. The light from each detector 4 and 5 is then passed through respective filters, 6 and 7, polarizers 8 and 9 and photomultiplier tubes 10 and 11. The output of the photomultipliers 10 and 11 are coupled to a two port clockcounter 12. The clockcounter 12 is designed to count the pulsed output from the photomultiplier tubes 10 and 11 over a specified time period and has circuitry designed to compute the ratio of the fluorescence from the detectors. This ratio is a measure of the degree of rotation of the fluorophore in the polymer. Optionally, the clockcounter 12 may have an output which goes to a comparator 13 or may have a built-in circuit which acts as a comparator to compare the measured degree of rotation of the fluorescent material within the polymer with that of a desired standard or a preset level. The comparator can then activate a switch or circuit to control means 14 for inducing polymerization, such as a light source or heat source, as the case may be, to continue polymerization until the desired degree of cure is achieved. It is preferred that the laser or other source of activating radiation impinge the film at a 45° angle relative to the surface of the film.

It should be remembered that the degree of rotation or polarization of the fluorescent material is a measure of the degree of polymerization or cure of the polymer and hence, the measurement of the degree of rotation or polarization can be used effectively to control the polymer cure.

The novel method will be demonstrated from the results of an investigation of dielectric materials used in printed circuit board applications. Specifically, photopolymeric dielectric materials used in multilayer printed circuit boards have been investigated. These materials are complex mixtures of acrylate terminated acrylonitrile-butadiene rubbers, epoxy-acrylated resins and a variety of vinyl monomers. Examples of such mixtures as used for multilayer printed circuit boards can be found with reference to U.S. Pat. No. 4,511,757 which issued on Apr. 16, 1985 to J. A. Ors and R. D. Small. The degree of cure of these photopolymers have been determined by measuring changes in polarization values on films that have been subjected to variations in the imaging process, such as variations in radiation time and intensity, development time and post hard-cure bake time and temperature. Further, the effect of the addition of varying quantities of a crosslink agent, trimethyloxypropane triacrylate (TMPTA), on the degree of cure was also determined. The resulting polarization values were compared with measurements of the degree of cure obtained from determining the % Sol and from $T_g$ data, both destructive methods for determining the degree of cure. The particular polymer mixtures which have been studied are given in Table 1. Films of these mixtures were coated on aluminum panels with a 24-thread-per-inch draw bar which yields films of about 5 mils thick.

TABLE 1

| MIXTURES | COMPONENTS (weight %) | | | | | | | | |
|---|---|---|---|---|---|---|---|---|---|
| | RDX 1 | RDX 2 | IBOA | NVP | TMPTA | DMPA | Dye (X-1163-9) | Pigment | PRODAN |
| 1 | 40.3 | 23.0 | 17.2 | 16.1 | — | 1.6 | 0.4 | 0.4 | |
| 2 | 38.2 | 22.0 | 16.4 | 15.4 | 5.0 | 1.5 | 0.48 | 1.5 | |
| 3 | 36.6 | 21.0 | 15.6 | 14.7 | 9.1 | 1.5 | 0.46 | 1.5 | |
| 4 | 35.0 | 20.0 | 15.0 | 14.1 | 13.0 | 1.4 | 0.44 | 1.4 | |
| A | — | 48.6 | 32.5 | 14.9 | — | 2.0 | — | — | 1.0 |
| B | — | 48.2 | 31.6 | 16.3 | — | 2.0 | 1.0 | — | |
| C | — | 48.2 | 30.6 | 17.9 | — | 2.0 | — | — | |

In accordance with the notations in the above table RDX 1 is a rubber modified epoxy acrylate; RDX 2 is an epoxy acrylated resin; IBOA is isobornyl acrylate; NVP is N-vinylpyrrolidone; TMPTA is trimethyloxypropane triacrylate; DMPA is dimethoxy phenylacetophenone; the fluorescent dye is Aldrich No. X-1163-9, a diglycidyl derivative of 4-amino-1,8-naphthalimide; the pigment for mixtures 1 through 4 is a green Penn Color pigment and PRODAN, a fluorescent dye, is 6-Propionyl-2-(dimethylamino)naphthalene.

In order to measure the extent of cure of these photodefinable mixtures as used in multilayer printed circuit board technology, the polymer films were imaged by means of either a low intensity light source, e.g., a 500 Watt mercury arc source with an output of 1 milliwatt per square centimeter or a high intensity light source, e.g., a 2000 Watt mercury arc source with an output of 11 milliwatt per square centimeter. The imaged films were developed with 1,1,1-trichloroethane as a development solvent. The radiation times used compare with those radiation times necessary to obtain 6 mil vias in the photodefinable dielectric. These times were 5 seconds on the high intensity imaging and 13 seconds with the low intensity imaging source.

The degree of cure as measured by polarization measurements was compared with Sol fraction data obtained from the extraction of the films in methylene chloride and reported as 1-% Sol. The glass transition temperature of the films was measured on a Dupont-1090 with a 943 Thermal Mechanical Analyzer module using an expansion probe.

Figure 2:
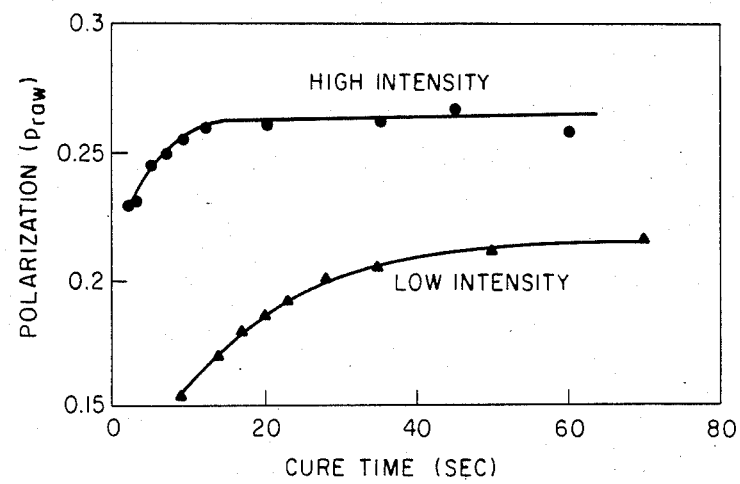
FIG. 2 is a graph indicating the measure of cure by polarization values as a function of photopolymer cure time for a photopolymer cured at both high and low intensity radiations.
Figure 3:
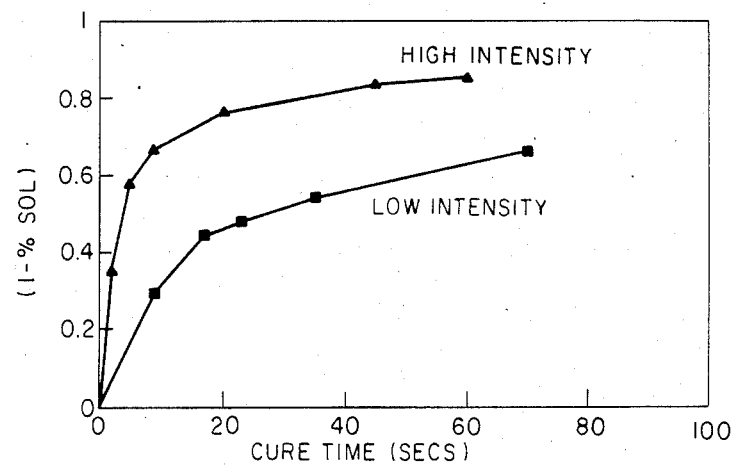
FIG. 3 is a graph showing the measure of cure of a photopolymer as a function of cure time for the same polymers as shown in FIG. 1, but determined as a function of percent of solubility (destructive solvent extraction test)
Figure 4:
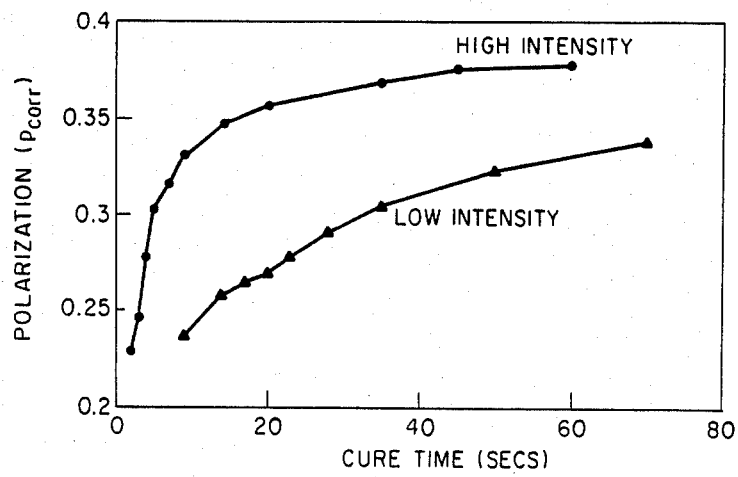
FIG. 4 is a replot of FIG. 2 correcting the polarization value for film thickness.

Referring to FIG. 2 there is shown a graph indicating the measure of cure of films prepared from Mixture No. 1 as determined by polarization measurements as a function of photopolymer cure time for a photopolymer cured with both high and low intensity radiation. FIG. 3 is a similar graph which shows the measure of cure for the same system, but determined as a function of % Sol. As can be seen from comparing FIGS. 2 and 3, the measure of the degree of cure achieved as a function of cure time by raw polarization data and from % Sol data are comparable. In fact, the data compares even more closely when the polarization measurements are corrected for film thickness as shown in FIG. 4.

Figure 5:
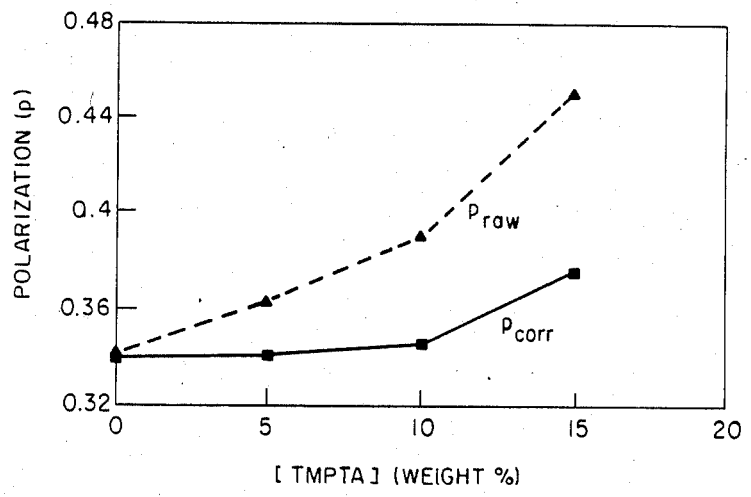
FIG. 5 is a graph indicating the degree of cure from polarization measurements as a function of the weight percent TMPTA added to a base polymer system.

The method was also evaluated by determining the degree of cure of mixture No. 1 with increasing amounts of TMPTA (mixtures 2-4) added to the mixture (see Table 1). All films were cured using the same curing times and power densities of U-V cure radiation. As can be seen with reference to FIG. 5, as expected, the amount of polarization and hence, the degree of cure increases with added TMPTA, a crosslinking agent. Also, at 15% TMPTA, the limiting value of polarization of the dye which relates to the total absence of rotational motion, and hence, a high degree of polymer crosslinking, is nearly reached. Also, the measure of the degree of crosslinking obtained from the polarization data follows that obtained from measurement of the $T_g$.

Figure 6:
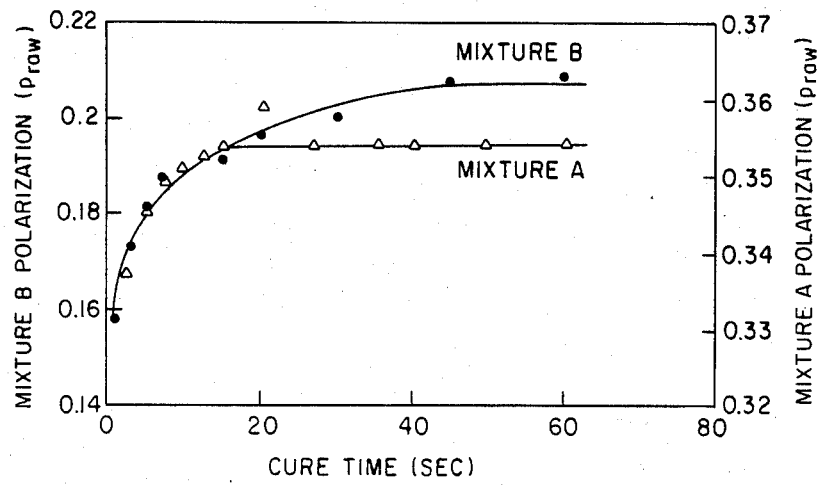
FIG. 6 is a graph indicating the degree of cure of a polymer as a function of cure time as determined by polarization measurements.

In addition to evaluating the method in systems which exhibit complex interactions between components, systems referred to in Table 1 as mixtures A, B & C were also examined. These systems eliminate the rubber-modified epoxy constituents which should negate any interaction which may occur between the fluorophore and the acrylonitrile or unsaturated groups. Mixture A differs from mixture B essentially in the fluorophore employed. PRODAN is a single, small size (MW-227) fluorophore having a relatively large dipole moment and is subject to changes in emission maximum based upon the polarity of its environment. The polarization results of films made from these mixtures are shown in FIG. 6. It can be seen that both the initial and final polarization values are lower and the curvature less steep than with mixture No. 1.

It should be noted that the method is not limited to the use of any particular fluorophore nor to measuring the extent of cure or control of cure of any particuar type of polymer. Further, the method is operable whether or not the polymer is a free film or on a substrate and is independent of the nature of the substrate.

In addition, it should be understood that the fluorophore may be part of the polymer as a pendant group bonded to the polymer as well as a separate compound.

What is claimed is:

1. A non-destructive method of measuring the degree of cure of a polymer system having a fluorophore therein comprises:
   (a) exciting the fluorophore in the polymer with linearly or plane polarized radiation;
   (b) collecting the fluorescent emission from the fluorophore at two predetermined angles with respect to the exciting radiation;
   (c) comparing the relative fluorescent emission from each of the two collecting angles so as to determine the degree of polarization or anisotropy of the fluorophore in the polymer; and
   (d) determining the degree of cure of the polymer from changes in the degree of polarization or anisotropy of the fluorophore.

2. The method set forth in claim 1, wherein the cured polymer is in the form of a film.

3. The method set forth in claim 1, wherein the fluorophore is added as a separate component to the polymer system.

4. The method set forth in claim 1, wherein the fluorophore is pendant to the polymer chain.

5. The method recited in claim 1, wherein the fluorophore is excited with a laser.

6. The method recited in claim 1, wherein the fluorescent emission is collected by a fiber optic detector and including the steps of passing the detected radiation through a polarizer and photomultiplier to a dual port clock-counter for comparing the collected emissions.

7. The method recited in claim 1, wherein the polymer is a film on a substrate and wherein the exciting radiaton impinges the polymer at an angle of about 45° from the axis perpendicular to the plane of the substrate.

8. A non-destructive method for measuring and controlling the degree of cure of a polymer having a fluorophore therein comprises:
   (a) exciting the fluorophore with linearly or plane polarized radiation;
   (b) collecting the fluorescent emission from the fluorophore at two predetermined angles with respect to the exciting radiation;
   (c) determining the degree of polarization or anisotropy of the fluorophore from its fluorescent emission;
   (d) comparing the degree of polarization or anisotropy determined with a predetermined value or standard; and
   (e) controlling means for inducing curing of the polymer in response with the measured comparison.

9. The method recited in claim 8, wherein said means for inducing curing of the polymer is controlled by an output from a comparator and wherein said means is selected from UV radiation or heat means.

10. The method recited in claim 8, wherein said polymer is in the form of a film or continuous web.

11. The method recited in claim 8, wherein the fluorophore is present as a separate component mixed with the polymer.

12. The method recited in claim 8, wherein the fluorophore is part of the polymeric molecule being pendant to the polymer chain.

13. The method recited in claim 8, wherein the fluorophore is excited by means of a laser.

14. The method recited in claim 8, wherein the polymer is on an opaque substrate and the exciting radiation is on a 45° angle incident to the substrate.

* * * * *